United States Defensive Publication [19] (H) [11] T964,007

Bailey et al. [43] Nov. 1, 1977

[54] ANTIMICROBIAL ESTERS OF ALIPHATIC DIOLS

[76] Inventors: August V. Bailey, 4470 San Marco Road, New Orleans, La. 70129; Gordon J. Boudreaux, 6625 Dorian St., New Orleans, La. 70126; Gene Sumrell, 1540 Aviators St., New Orleans, La. 70122; Arthur F. Novak, 656 College Hill Drive, Baton Rouge, La. 70808

[21] Appl. No.: 768,807

[22] Filed: Feb. 15, 1977

Related U.S. Application Data

[62] Division of Ser. No. 667,055, March 15, 1976, Pat. No. 4,024,164.

[51] Int. Cl.[2] ..... C09F 5/08; C09F 7/10

[52] U.S. Cl. ..... 260/410.5; 560/112

[57] ABSTRACT

New mixed esters of diols having one hydroxyl group esterified with benzoic acid and the other esterified with various saturated or unsaturated aliphatic acids or aromatic acids other than benzoic are found to have antimicrobial activity against several pathogenic microorganisms, and to have properties making them useful as antimicrobial agents.

11 Claims, No Sheets Drawing,

12 Pages Specification

The file of this unexamined application may be inspected and copies thereof may be purchased (849 O.G. 1221, Apr. 9, 1968).